United States Patent
Weiner et al.

(10) Patent No.: US 8,610,562 B2
(45) Date of Patent: Dec. 17, 2013

(54) AUTOMATIC DETERMINATION OF LOCATION FOR ETHERNET DEVICES

(75) Inventors: Herbert S. Weiner, Portland, OR (US); Eric G. Petersen, Aloha, OR (US); Brian T. Moons, Sherwood, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 640 days.

(21) Appl. No.: 12/697,831

(22) Filed: Feb. 1, 2010

(65) Prior Publication Data

US 2011/0187526 A1 Aug. 4, 2011

(51) Int. Cl.
*G08B 1/08* (2006.01)
(52) U.S. Cl.
USPC .................. 340/539.13; 340/8.1; 600/300
(58) Field of Classification Search
USPC .......... 340/539.13, 539.12, 8.1; 600/300, 301
See application file for complete search history.

(56) References Cited

U.S. PATENT DOCUMENTS

| | | | |
|---|---|---|---|
| 5,319,363 A | 6/1994 | Welch | |
| 5,500,854 A * | 3/1996 | Uotila | 370/254 |
| 6,414,635 B1* | 7/2002 | Stewart et al. | 342/457 |
| 7,316,648 B2* | 1/2008 | Kelly et al. | 600/300 |
| 7,881,945 B2* | 2/2011 | Schmitt et al. | 705/1.1 |
| 7,962,544 B2* | 6/2011 | Torok et al. | 709/200 |
| 8,102,254 B2* | 1/2012 | Becker et al. | 340/539.12 |
| 8,195,478 B2* | 6/2012 | Petersen et al. | 705/2 |
| 2005/0033124 A1* | 2/2005 | Kelly et al. | 600/300 |
| 2005/0190053 A1* | 9/2005 | Dione | 340/500 |
| 2006/0288095 A1* | 12/2006 | Torok et al. | 709/223 |
| 2008/0221918 A1* | 9/2008 | Petersen et al. | 705/2 |
| 2011/0148624 A1* | 6/2011 | Eaton et al. | 340/539.13 |

* cited by examiner

*Primary Examiner* — Eric M Blount
(74) *Attorney, Agent, or Firm* — Merchant & Gould P.C.

(57) ABSTRACT

A method for automatically locating an Ethernet patient monitor in one or more buildings includes querying, by a computing device of a central monitoring system, a switch using a Media Access Control address of the patient monitor, and receiving a port number to which the patient monitor is connected from the switch. The method also includes consulting a configuration file to determine a location of the patient monitor, and displaying a representation of the location of the patient monitor on a user interface representing at least a portion of the one or more buildings.

16 Claims, 4 Drawing Sheets

AUTOMATIC DETERMINATION OF LOCATION FOR ETHERNET DEVICES

BACKGROUND

The physical location of a device that is connected to a network can be an important piece of information. For example, in the hospital context, monitors are used to track the vital statistics of patients. The location of these patient monitors can be important, particularly when the patient monitors are connected to a central monitoring system that is remotely located from the monitors. When a patient monitor provides signals to the central monitoring system indicating that a patient needs attention, it is important that the caregiver can readily identify the location of the patent monitor and associated patient so that the caregiver can provide assistance.

In today's computing environment, many networks are Ethernet-based and support simultaneous sessions to multiple endpoints over such protocols as Transmission Control Protocol (TCP) and User Datagram Protocol (UDP). In such networks, there is no easy way to identify the physical location of a patient monitor in the network. Such systems either require monitors that are fixed within a given room, or require the caregiver to always update location information when the patient monitor is moved to a new location. Such scenarios can lead to an inflexible deployment of monitors and/or human error.

SUMMARY

One aspect relates to a method for automatically locating an Ethernet patient monitor in one or more buildings includes querying, by a computing device of a central monitoring system, a switch using a Media Access Control address of the patient monitor, and receiving a port number to which the patient monitor is connected from the switch. The method also includes consulting a configuration file to determine a location of the patient monitor, and displaying a representation of the location of the patient monitor on a user interface representing at least a portion of the one or more buildings.

In another aspect, a method for automatically locating an Ethernet patient monitor in one or more buildings includes: receiving, by a computing device of a central monitoring system, a rendezvous request from a patient monitoring device; consulting a configuration file to determine whether or not a switch is handled by the central monitoring system; querying the switch by sending a Simple Network Management Protocol Management Information Base query using a Media Access Control address of the patient monitor received in the rendezvous request; receiving a port number to which the patient monitor is connected from the switch; consulting the configuration file to determine whether or not the port is handled by the central monitoring system; establishing communication with the patient monitor; consulting a configuration file to determine a location of the patient monitor using coordinates in the configuration file; displaying a representation of the location of the patient monitor on a user interface representing at least a portion of the one or more buildings; and altering a state of the representation of the location of the patient monitor on the user interface based on the status of the patient monitor.

In yet another aspect, a patient monitoring system includes a patient monitor configured to measure one or more physiological characteristics of a patient, the patient monitor being connected to an Ethernet jack, and a switch including at least one port, the Ethernet jack being connected to the port. The system also includes a central monitoring system including a processor, and a memory encoding instructions that, when executed by the processor, cause the processor to: query the switch using a Media Access Control address of the patient monitor; receive a port number to which the patient monitor is connected from the switch; consult a configuration file to determine a location of the patient monitor; and display a representation of the location of the patient monitor on a user interface representing at least a portion of one or more buildings.

The details of one or more techniques are set forth in the accompanying drawings and the description below. Other features, objects, and advantages of these techniques will be apparent from the description, drawings, and claims.

DETAILED DESCRIPTION

The present application is directed to the automatic determination of the location of devices connected to a network. In examples described herein, the devices are patient monitoring devices that are connected to a central monitoring system through a network. The location of the devices within a building or buildings, such as a hospital or clinic, is automatically determined so that caregivers at the central monitoring system can readily identify the location of a patient in need. Although the examples provided herein are described in reference to a patient monitoring system, the principles are applicable to other scenarios as well.

Figure 1:
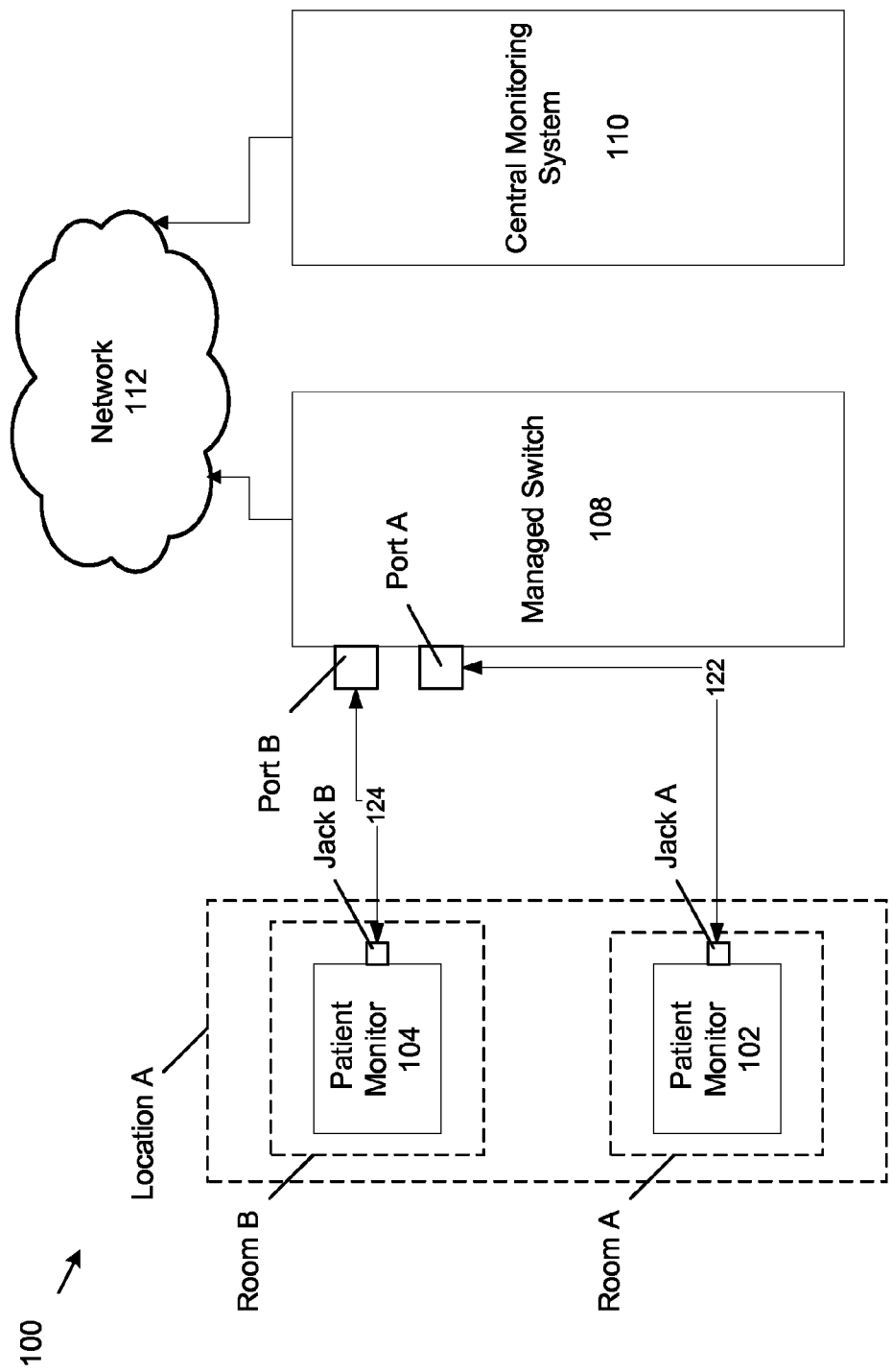
FIG. 1 shows an example patient monitoring system.

Referring now to FIG. 1, an example patient monitoring system 100 is shown. In example embodiments, the patient monitoring system 100 is an ACUITY® Central Monitoring System from Welch Allyn Inc. of Skaneateles Falls, N.Y. Other systems and configurations are possible.

The patient monitoring system 100 utilizes a plurality of portable patient monitors 102, 104 that are positioned in different locations within a Location A, such as a hospital or clinic. In the example shown, the patient monitor 102 is currently located in Room A, and the patient monitor 104 is currently located in Room B of the Location A. In other examples, more or fewer monitors, locations, and/or rooms can be used.

The patient monitors 102, 104 are used to measure physiological information associated with a patient located in the Rooms A and B. For example, in one embodiment, the patient monitors 102, 104 monitor temperature, oxygen saturation, heart rate, and blood pressure for a patient. One example of such a patient monitor is the PROPAQ® CS monitor from Welch Allyn Inc. of Skaneateles Falls, N.Y. In other examples, other parameters and types of monitor devices can be used.

The patient monitors 102, 104 are each connected to a network jack A, B located in each of the Rooms A and B. In this example, the network jacks A, B are Ethernet jacks. The network jacks A, B are, in turn, connected by cables 122, 124 to a managed switch 108.

The managed switch 108 includes a plurality of ports, each port accepting an Ethernet cable. In one example, the managed switch 108 is a Catalyst 2960 managed switch manufactured by Cisco Systems of San Jose, Calif. Other configurations are possible.

In the example shown, the cable 122 is connected to a port A and the cable 124 is connected to the port B of the managed switch 108. The cables 122, 124 are tracked during installation so that it is known that the cable 122 originates in the Room A, and the cable 124 originates in the Room B. In this manner, it is known that the port A of the managed switch 108 is connected to the cable 122 that originates in the Room A, and the port B is connected to the cable 124 originates in the Room B.

The managed switch 108 is, in turn, connected to a central monitoring system 110 through a network 112, such as a local area network (LAN) or wide area network (WAN). Other types of networks are possible. In example embodiments, the central monitoring system 110 is an ACUITY® Central Station monitoring system from Welch Allyn Inc. of Skaneateles Falls, N.Y. Other types of computing devices can also be used.

In the example shown, the central monitoring system 110 is programmed to remotely monitor the status of the patient monitors 102, 104. The central monitoring system 110 includes one or more displays that allow caregivers to review patient information gathered by the patient monitors 102, 104. In some examples, the central monitoring system 110 also provides alarm information so that acute situations can be addressed by the caregiver in a timely manner.

Figure 2:
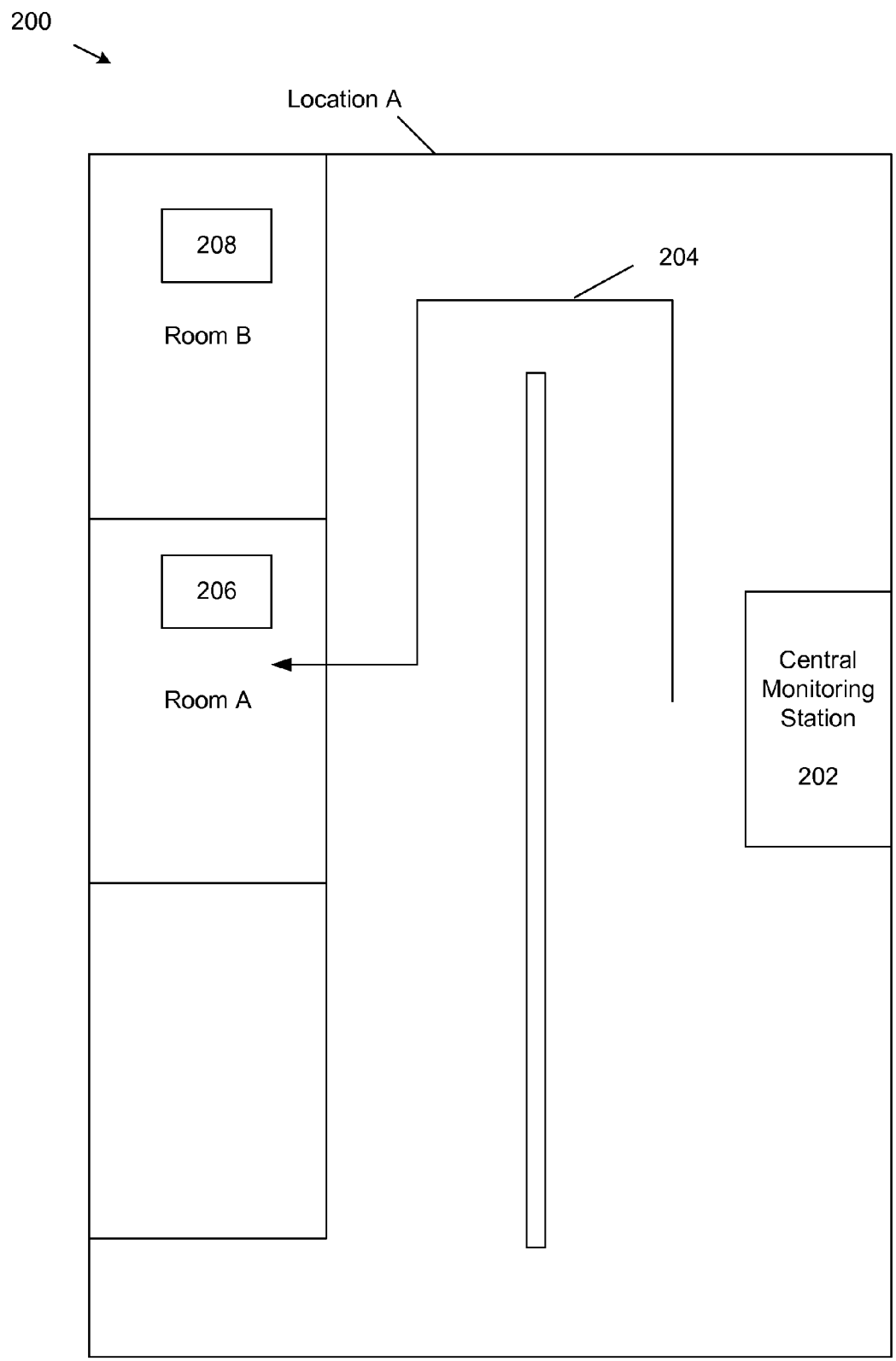
FIG. 2 shows an example graphical user interface of the patient monitoring system of FIG. 1.

For example, referring now to FIG. 2, an example graphical user interface 200 of the central monitoring system 110 is shown. The interface 200 provides a representation of a portion of a hospital or clinic, such as the Location A of FIG. 1. The interface 200 shows a central monitoring station 202 and the Rooms A and B. A caregiver at the central monitoring station 202 can use the central monitoring system 110 to receive physiological data associated with the patients located in the Rooms A and B as measured by the patient monitors 102, 104.

If the central monitoring system 110 provides an alarm condition in which the caregiver is needed in a particular room, such as the Room A, the interface 200 provides the caregiver with a route 204. The route 204 provides the caregiver with the most efficient directions to reach the Room A as quickly as possible.

In example embodiments, the patient monitoring system 110 can automatically determine when a patient monitor, such as the patient monitors 102, 104, is connect to the patient monitoring system 100. Location information and patient status are displayed in the interface 200.

For example, an icon 206, 208 representing the patient monitors 102, 104 on the interface 200 changes from green to red when the patient goes into an alarm condition. If a patient monitor is inadvertently disconnected, the icon 206, 208 representing the patient monitor 102, 104 on the hospital floor plan changes from green to yellow, to indicate an equipment alert state. Other types of alarming and configurations can be used. In this manner, the location of the patient monitors 102, 104 can be automatically determined so that a caregiver to easily locate the associated patient during an alarm condition, as described further below.

Figure 3:
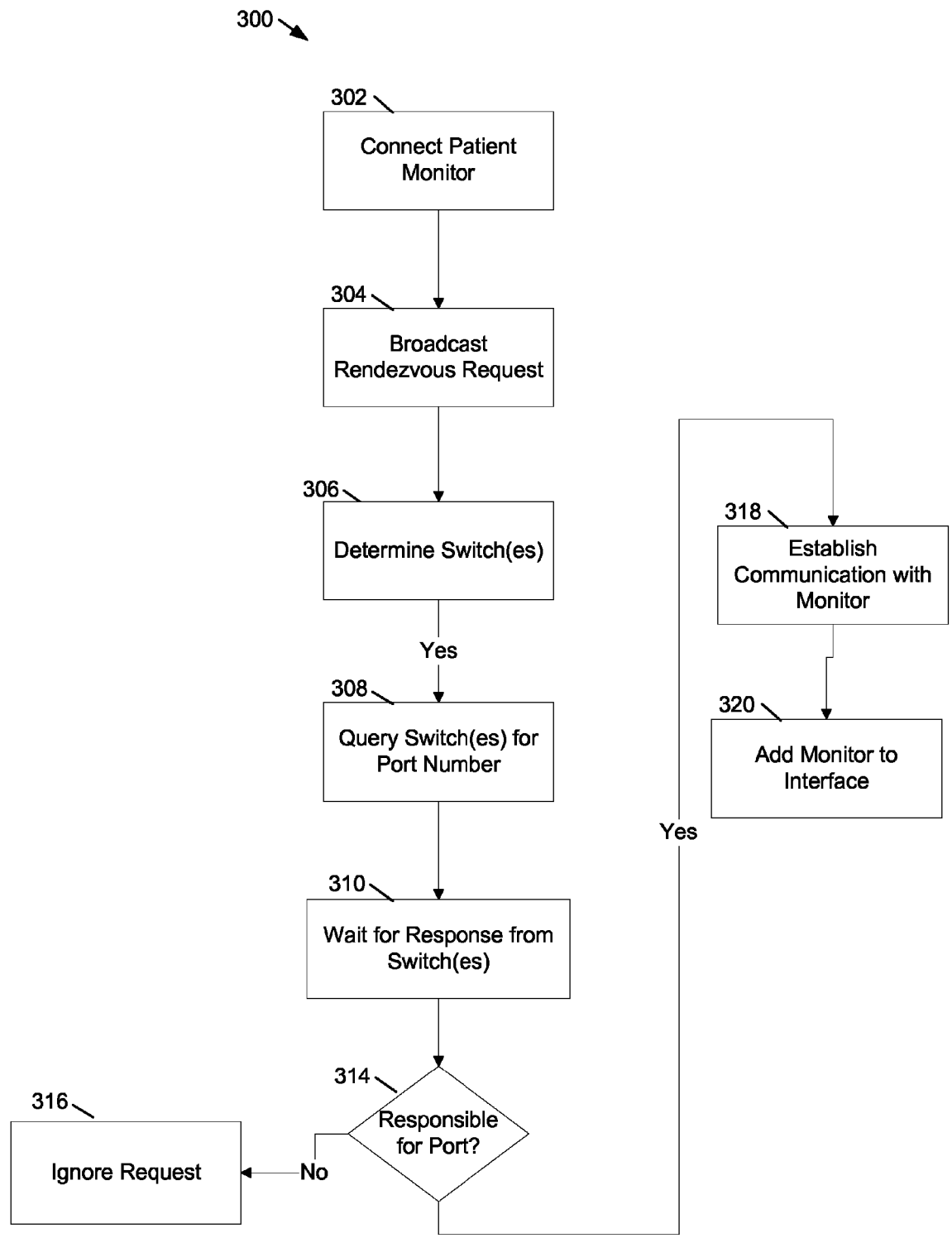
FIG. 3 shows an example method for automatic determination of location of a device.

Referring now to FIG. 3, an example method 300 for automatically determining the location of a patient monitor is shown.

Initially, at operation 302, a patient monitor (e.g., the patient monitor 102) is connected to an Ethernet jack. Upon connection, the patient monitor uses Dynamic Host Configuration Protocol (DHCP) to request an IP address, if the monitor has not already been assigned a static IP address.

Next, the patient monitor 102 broadcasts an Ethernet rendezvous request to a known UDP port (7711) at operation 304. The Media Access Control (MAC) Address of the patient monitor 102 requesting the rendezvous is embedded in the rendezvous request packet. The request is relayed through the managed switch 108 to the central monitoring system 110.

Upon receipt of the rendezvous packet, the central monitoring system 110 consults a configuration file to determine for which switch or switches the central monitoring system 110 is responsible at operation 306.

Next, at operation 308, the central monitoring system 110 queries the switch or switches identified in the configuration file to determine if any of the switches have a port associated with the MAC address in the rendezvous request. In one example, the central monitoring system 110 queries the managed switch 108 using the Simple Network Management Protocol (SNMP) to identify the port to which the MAC address of the patient monitor that sent the rendezvous request is connected. For example, a standard SNMP Management Information Base (MIB) query, such as RFC 1493, can be used to extract the necessary MAC address to port mapping information from the managed switch 108.

Next, at operation 310, the central monitoring system 110 waits for a response from the managed switch 108 reporting a port associated with the noted MAC address. If the managed switch 108 that is queried by the central monitoring system 110 does not have a port associated with the MAC address provided, the managed switch 108 will not respond. Alternatively, if the managed switch 108 does have a port associated with the MAC address provided, the managed switch 108 will respond with the port number.

In some systems, more than one managed switch 108 can be used. In such scenarios, the central monitoring system 110 can query multiple managed switches 108 listed in the central monitoring system 110 configuration file. Any of the manages switches 108 having a port number associated with the MAC address would then respond to the central monitoring system 110 with the port number.

Next, at operation 314, the central monitoring system 110 consults the configuration file again to determine if the central monitoring system 110 is responsible for that particular port on the managed switch 108. Specifically, the central monitoring system 110 compares the port number returned by the managed switch 108 to the configuration file to determine if it matches any of the ports listed in the file.

In addition, multiple central monitoring systems 110 can be used, with each central monitoring system 110 being programmed to perform the same sequence of steps described above to determine whether the patient monitor is connected to that central monitoring system, and if so, to determine the correct location of the patient monitor.

It is possible that more than one central monitoring system 110 is configured to be responsible for some or all network ports (locations). This results in a high availability configuration, in which multiple central monitoring systems 110 monitor the same patients, so that, in the event of a hardware or software failure of one central monitoring system 110, patients are still being monitored by a redundant central monitoring system 110.

In one example, the configuration file is stored on the central monitoring system 110. One entry from such an example configuration file is as follows.

| $ICON | 1312A | switch-one:20 | 378 209 | 441 272 459 254 |
| --- | --- | --- | --- | --- |

A configuration file typically would have multiple entries for multiple switches and/or multiple ports for each switch.

In the configuration file, the parameter "switch-one" indicates that the central monitoring system 110 is responsible for at least patient monitors connected to the managed switch 108 labeled "switch-one." The number "20" indicates the port on the managed switch 108 labeled "switch-one" for which the central monitoring system 110 is responsible.

If the managed switch 108 returns a port number other than "20" for the example given, control is passed to operation 316, and the central monitoring system 110 ignores the request. Alternatively, if the port number returned by the managed switch 108 is "20," control is passed to operation 318, and the central monitoring system 110 establishes communication with the patient monitor 102.

There are generally four possible scenarios for operations 310, 314:

(a) None of the managed switches queried by the central monitoring system responds with a port number associated with the MAC address. In this scenario, this central monitoring system is not responsible for the location to which the patient monitor is connected, although another central monitoring system on the same network may be responsible for the patient monitor.

(b) One or more of the managed switches responds with a port number, but the configuration file indicates that the central monitoring system is not responsible for any of those port numbers on those managed switches. In this scenario, the central monitoring system is not responsible for the location to which the patient monitor is connected. (Multiple managed switches could respond because a switch might respond if the MAC address is indirectly reachable through that switch even if it is not directly connected to that switch, such as intermediate switches/routers as further described below. Ports listed in the configuration file should be connected directly to the room number and not to any other switch.) As in (a), another central monitoring system on the same network may be responsible for the patient monitor.

(c) One managed switch responds with a port number for which the central monitoring system is responsible, based upon the configuration file. In this scenario, based upon the port number, the central monitoring system can identify the location of the patient monitor, and can proceed to initiate a connection to the patient monitor. In this scenario, one or more other central monitoring systems can also report with port numbers for which this central monitoring system is not responsible (if, for example, there are one or more intermediate switches/routers), which are ignored by the central monitoring system.

(d) Multiple managed switches respond with a port number for which the central monitoring system is responsible. This would indicate a configuration error, since the patient monitor can only be directly connected to a single switch, and the configuration file should not include ports that are connected to other switches rather than directly to patient rooms.

Since the central monitoring system 110 now knows the port from the switch, the central monitoring system 110 consults the configuration file to determine a location of the patient monitor 102, so that the monitor 102 can be added to the interface at operation 320. Specifically, the entry "1312A" in the configuration file provides the room number for the network jack to which the patient monitor 102 is plugged, such as the Room A. In addition, the entry "378 209" provides X, Y coordinates that allow the icon 206 to be placed on the interface 200 in the correct location. Using this information, the central monitoring system 110 adds the location of the monitor to the user interface 200.

Other information is also provided in the configuration file. For example, the entry "$ICON" is a keyword that determines the type of icon 206 that is placed on the user interface 200 to represent the patient monitor 102. As noted above, the icon 206 can be color-coded to indicate a state of the patient monitor 102. When originally connected, the icon 206 is blue until communication is established. At that point, the icon 206 is changed to yellow until patient information (e.g., from a patient database) is provided. Once communication is established and patient information is identified, the icon 206 color is green. The icon 206 can change to red to indicate an alarm status. Other coding schemes can be used.

The coordinates "441 272 459 254" provide coordinates that allow the most efficient route 204 from the central monitoring system 110 to the location of the patient monitor 102 to be plotted on the interface 200.

In one example, each of the Ethernet patient monitors 102, 104 is configured to automatically switch to a different port and send out a new rendezvous request upon detecting that the monitor 102, 104 has been disconnected from the central monitoring system 110. This assures that the central monitoring system 110 identifies when the Ethernet patient monitors 102, 104 have been moved to different locations.

In addition to polling upon receipt of a rendezvous request, the central monitoring system 110 can also periodically poll the managed switch 108 to determine whether or not a patient monitor with a new MAC Address is associated with one of the ports of the managed switch 108, or also to determine if a patient monitor has been disconnected from a port. For example, the central monitoring system 110 periodically polls the managed switch 108 to determine if the MAC Address of a particular monitor is still attached to a particular port on the switch. If not, the central monitoring system 110 can determine that the patient monitor has been disconnected and update the user interface 200 accordingly. For example, the icon used to represent the patient monitor can be changed from a green to a yellow color to indicate that the monitor is no longer connected and providing updates.

In this manner, the Ethernet patient monitors 102, 104 can be can be deployed in multiple rooms in the hospital where suitable network jacks are located and can be moved from room to room or unit to unit as patient monitoring demands change. The patient monitoring system 100 can automatically determine the location of each monitor when it is connected to the system without requiring manual intervention. This increases flexibility, efficiency, and accuracy for the system. Furthermore, when a patient monitor is moved from one room to a different room monitored by the same central monitoring system or a different central monitoring system, the central monitoring system(s) can automatically update the location of the patient, if any, connected to that patient monitor.

In addition, the configuration can be modified as the patient monitoring system 100 grows or changes. The configuration files can be changed if the layout of the hospital is modified or if additional switches and/or central monitoring systems are added to the hospital. For example, if a new room is added to the hospital, the configuration file can be modified to provide the location, switch, port, and other information associated with the new room. When a monitoring device is connected to the network jack in the new room, the central monitoring system can consult the updated configuration file to determine the location of the monitor in the new room.

Further, the monitoring can occur even if the managed switch is not connected directly to the central monitoring system (e.g., separated by one or more intermediate switches/ routers). The Ethernet rendezvous request packets and the SNMP requests and responses can be forwarded to the intermediate switches and routers.

Figure 4:
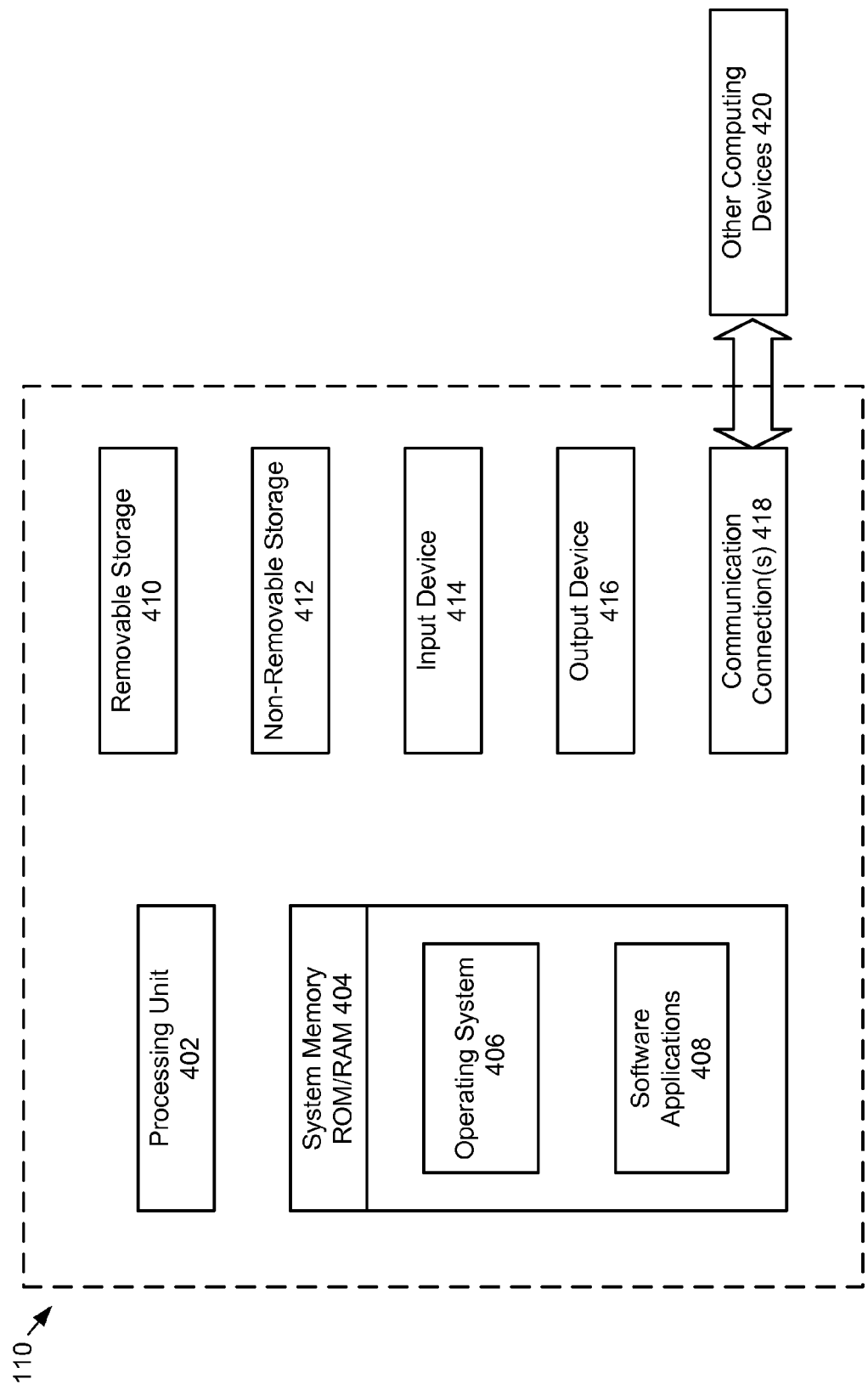
FIG. 4 shows example components of a computing device of the patient monitoring system of FIG. 1.

Referring now to FIG. 4, example components of the central monitoring system 110 are shown. In example embodiments, the central monitoring system 110 is a computing device. The central monitoring system 110 includes input/output devices, a central processing unit ("CPU"), memory, and a network device. The patient monitors 102, 104 and the managed switch 108 can be configured in a similar manner.

In a basic configuration, the central monitoring system 110 typically includes at least one processor or processing unit 402 and system memory 404. The system memory 404 can include computer readable media. Computer readable media can include both computer readable storage media and communication media.

Computer readable storage media is physical media, such as data storage devices (removable and/or non-removable) including magnetic disks, optical disks, or tape. Such additional storage is illustrated in FIG. 4 by removable storage 410 and non-removable storage 412. Computer readable storage media may include volatile and nonvolatile, removable and non-removable media implemented in any method or technology for storage of information, such as computer readable instructions, data structures, program modules, or other data. Computer readable storage media can include, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by central monitoring system 110. Any such computer readable storage media may be part of device 102.

Communication media may typically be embodied by computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media.

System memory 404 typically includes an operating system 406 suitable for controlling the operation of a networked personal computer, such as the Solaris (Unix) operating system from Sun Microsystems of Santa Clara, Calif. Other operating systems, such as WINDOWS® operating systems from Microsoft Corporation of Redmond, Wash., or other Linux operating systems can be used. The system memory 404 also includes one or more software applications 408 and may include program data.

Central monitoring system 110 may also have input device(s) 414 such as keyboard, mouse, pen, voice input device, touch input device, etc. Output device(s) 416 such as a display, speakers, printer, etc. may also be included. The central monitoring system 110 may also contain communication connections 418 that allow the device to communicate with other computing devices 420 (e.g., managed switch 108), such as over a network in a distributed computing environment, for example, an intranet or the Internet.

The various embodiments described above are provided by way of illustration only and should not be construed to limiting. Various modifications and changes that may be made to the embodiments described above without departing from the true spirit and scope of the disclosure.

What is claimed is:

1. A method for automatically locating an Ethernet patient monitor in one or more buildings, the method comprising:
    querying, by a computing device of a central monitoring system, a switch comprising a plurality of ports, the patient monitor being connected to one of the plurality of ports, a Media Access Control address of the patient monitor being included in the query;
    receiving from the switch a port number of the switch to which the patient monitor is connected, the port number being associated with the Media Access Control address;
    using first coordinates in a configuration file to determine a location of the patient monitor based on the port number;
    displaying a representation of the location of the patient monitor on a user interface representing at least a portion of the one or more buildings;
    using second coordinates in the configuration file to identify a route from the central monitoring system to the location of the patient monitor, the second coordinates being different from the first coordinates; and
    displaying the route on the user interface.

2. The method of claim 1, further comprising:
    receiving a rendezvous request from the patient monitoring device; and
    consulting the configuration file to determine whether or not the switch is handled by the central monitoring system.

3. The method of claim 1, further comprising establishing communication with the patient monitor.

4. The method of claim 1, further comprising consulting the configuration file to determine whether or not the port is handled by the central monitoring system.

5. The method of claim 1, wherein querying the switch further comprises sending a Simple Network Management Protocol Management Information Base using the Media Access Control address of the patient monitor.

6. The method of claim 1, further comprising altering a state of the representation of the location of the patient monitor on the user interface based on the status of the patient monitor.

7. The method of claim 1, further comprising periodically querying the switch to identify any ports of the switch having a new patient monitor with a new Media Access Control address associated therewith.

8. The method of claim 7, further comprising identifying the new patient monitor based upon the new Media Access Control address returned by the switch.

9. The method of claim 8, further comprising:
    consulting the configuration file to determine a second location of the new patient monitor; and
    displaying a second representation of the second location of the new patient monitor on the user interface.

10. The method of claim 1, further comprising periodically querying the switch to identify when the patient monitor is disconnected from a port associated with the port number of the switch.

11. The method of claim 10, further comprising updating the representation of the patient monitor on the user interface to indicate disconnection of the patient monitor.

12. A method for automatically locating an Ethernet patient monitor in one or more buildings, the method comprising:
    receiving, by a computing device of a central monitoring system, a rendezvous request from a patient monitoring device;

consulting a configuration file to determine whether or not a switch is handled by the central monitoring system;

querying the switch by sending a Simple Network Management Protocol Management Information Base using a Media Access Control address of the patient monitor received in the rendezvous request;

receiving a port number to which the patient monitor is connected from the switch;

consulting the configuration file to determine whether or not the port is handled by the central monitoring system;

establishing communication with the patient monitor;

using first coordinates in a configuration file to determine a location of the patient monitor using coordinates in the configuration file;

displaying a representation of the location of the patient monitor on a user interface representing at least a portion of the one or more buildings;

using second coordinates in the configuration file to identify a route from the central monitoring system to the location of the patient monitor, the second coordinates being different from the first coordinates, and the second coordinates including a string of two or more numbers, with each of the numbers representing a position on the map and the numbers being used to plot a path from the central monitoring system to the patient monitor;

displaying the route on the user interface; and altering a state of the representation of the location of the patient monitor on the user interface based on the status of the patient monitor.

13. The method of claim 12, further comprising periodically querying the switch to identify any ports of the switch having a new patient monitor with a new Media Access Control address associated therewith.

14. The method of claim 13, further comprising identifying the new patient monitor based upon the new Media Access Control address returned by the switch.

15. The method of claim 14, further comprising:

consulting the configuration file to determine a second location of the new patient monitor; and displaying a second representation of the second location of the new patient monitor on the user interface.

16. The method of claim 12, further comprising:

periodically querying the switch to identify when the patient monitor is disconnected from a port associated with the port number of the switch; and updating the representation of the patient monitor on the user interface to indicate disconnection of the patient monitor.

* * * * *